United States Patent [19]

Akai et al.

[11] Patent Number: 4,972,180

[45] Date of Patent: Nov. 20, 1990

[54] APPARATUS FOR DETERMINING RATE OF DISCHARGE FROM NOZZLE FOR SPRAYING AQUEOUS SOLUTION OF HYDROGEN PEROXIDE

[75] Inventors: Tadao Akai; Masato Shibata; Hiromichi Nishino, all of Kitajima, Japan

[73] Assignee: Shikoku Kakoki Co., Ltd., Tokushima, Japan

[21] Appl. No.: 290,230

[22] Filed: Dec. 27, 1988

[30] Foreign Application Priority Data

Dec. 29, 1987 [JP] Japan .......................... 62-201591[U]

[51] Int. Cl.$^5$ .......................... G01F 1/00; G08B 21/00
[52] U.S. Cl. .................................. 340/611; 340/606; 340/626; 73/861; 73/861.42; 73/861.61
[58] Field of Search .................. 340/611, 626, 606; 239/71, 72, 69; 73/861, 861.42, 861.52, 861.61, 861.63; 364/510

[56] References Cited

U.S. PATENT DOCUMENTS

| 3,665,959 | 5/1972 | Castillon | 73/199 |
| 4,130,017 | 12/1978 | Benedict | 73/861.61 |
| 4,253,093 | 2/1981 | Johanson | 340/606 |
| 4,285,245 | 8/1981 | Kennedy | 73/861 |
| 4,821,580 | 4/1989 | Jorritsma | 73/861.42 |

Primary Examiner—Joseph A. Orsino
Assistant Examiner—Kinfe-Michael Negash
Attorney, Agent, or Firm—Armstrong, Nikaido, Marmelstein, Kubovcik & Murray

[57] ABSTRACT

An apparatus for determining the rate of discharge from a nozzle for spraying an aqueous solution of hydrogen peroxide comprises a pressure sensor for detecting the internal pressure of a pipe for supplying the solution to the nozzle under elevated pressure, and means for determining the rate of discharge from the pressure detected by the pressure sensor and the predetermined relationship of the discharge rate of the nozzle with the internal pressure of the pipe.

4 Claims, 2 Drawing Sheets

APPARATUS FOR DETERMINING RATE OF DISCHARGE FROM NOZZLE FOR SPRAYING AQUEOUS SOLUTION OF HYDROGEN PEROXIDE

BACKGROUND OF THE INVENTION

The present invention relates to an apparatus for use in the field of packaging machines for foods and the like for determining the rate of discharge from a nozzle for spraying an aqueous solution of hydrogen peroxide, for example, to sterilize containers.

The rate of discharge from such a spray nozzle is usually determined from the rate of flow through a pipe for supplying a pressurized aqueous solution of hydrogen peroxide by measuring the flow rate with a flowmeter of the differential pressure type or electromagnetic flowmeter. However, since the amount of the solution flowing through the supply pipe is very small, it has been impossible to accurately measure the very small rate with any flowmeter and therefore to accurately determine the discharge rate. The reason is that the aqueous hydrogen peroxide solution releases oxygen when decomposed by exposure to heat, contact with impurities or the flow of itself, permitting the resulting oxygen to flow along with the solution.

Further since the solution is highly corrosive, the flowmeter must be ingeniously protected against corrosion. This encounters difficulties and requires an increased cost.

SUMMARY OF THE INVENTION

The main object of the present invention is to provide an apparatus free of the foregoing problems for determining the rate of discharge from a nozzle for spraying an aqueous solution of hydrogen peroxide.

The apparatus of the invention for determining the rate of discharge from a nozzle for spraying an aqueous solution of hydrogen peroxide comprises a pressure sensor for detecting the internal pressure of a pipe for supplying the solution to the nozzle under elevated pressure, and means for determining the rate of discharge from the pressure detected by the pressure sensor and the predetermined relationship of the discharge rate of the nozzle with the internal pressure of the pipe.

The apparatus of the invention is adapted to determine the discharge rate by detecting the internal pressure of the pipe for supplying the solution. Since the pressure is not affected by the presence or absence of oxygen evolved within the supply pipe, the discharge rate can be determined accurately.

DESCRIPTION OF THE PREFERRED EMBODIMENT

An embodiment of the invention will be described below with reference to the drawings.

Figure 1:
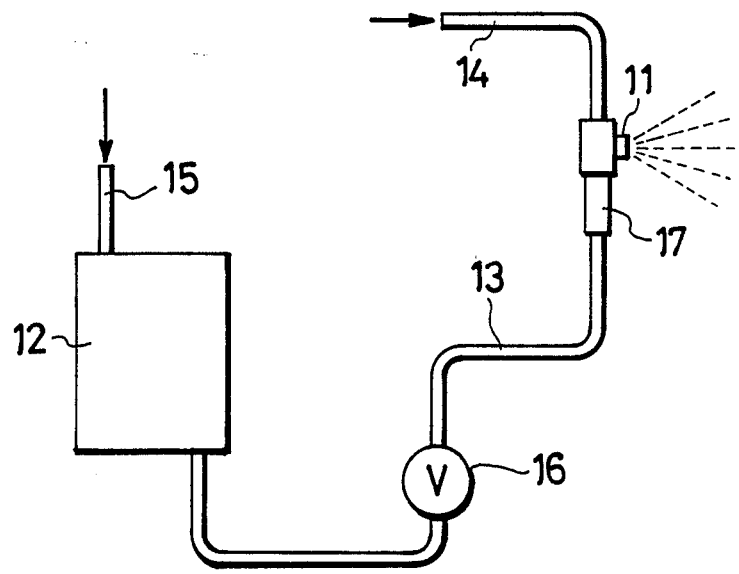
FIG. 1 is a diagram showing a spray system in its entirety which includes an apparatus of the invention.

FIG. 1 shows the construction of a system for spraying an aqueous solution of hydrogen peroxide.

A pipe 13 for supplying the solution extends from a tank 12 to a spray nozzle 11, which has connected thereto a pipe 14 for supplying air for use in spraying the solution. A pipe 15 for supplying pressurizing air is connected to the tank 12. The solution supply pipe 13 is provided with a valve 16 at an intermediate portion of its length for controlling very low flow rates and with a pressure sensor 17 adjacent to the nozzle 11.

Figure 2:
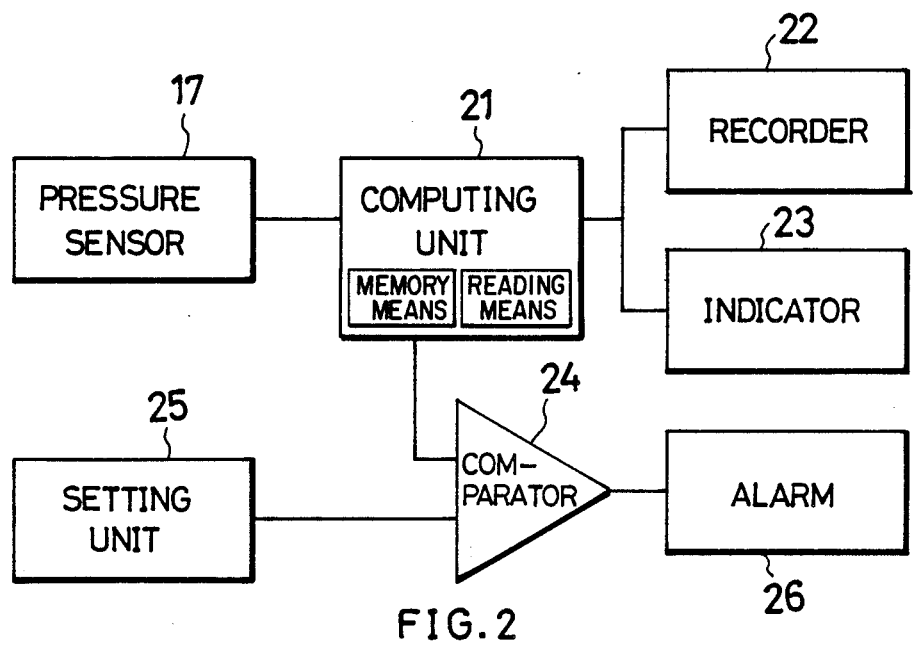
FIG. 2 is a block diagram showing the construction of the apparatus.

With reference to FIG. 2, the pressure detected by the pressure sensor 17 is fed to a computing unit 21. Although not shown, the computing unit 21 includes memory means 27 having stored therein the relationship of the discharge rate of the nozzle 11 with the internal pressure of the solution supply pipe 13, and reading 28 means for reading from the memory means the discharge rate corresponding to a particular pressure detected by the sensor 17 and delivering the read data.

Figure 3:
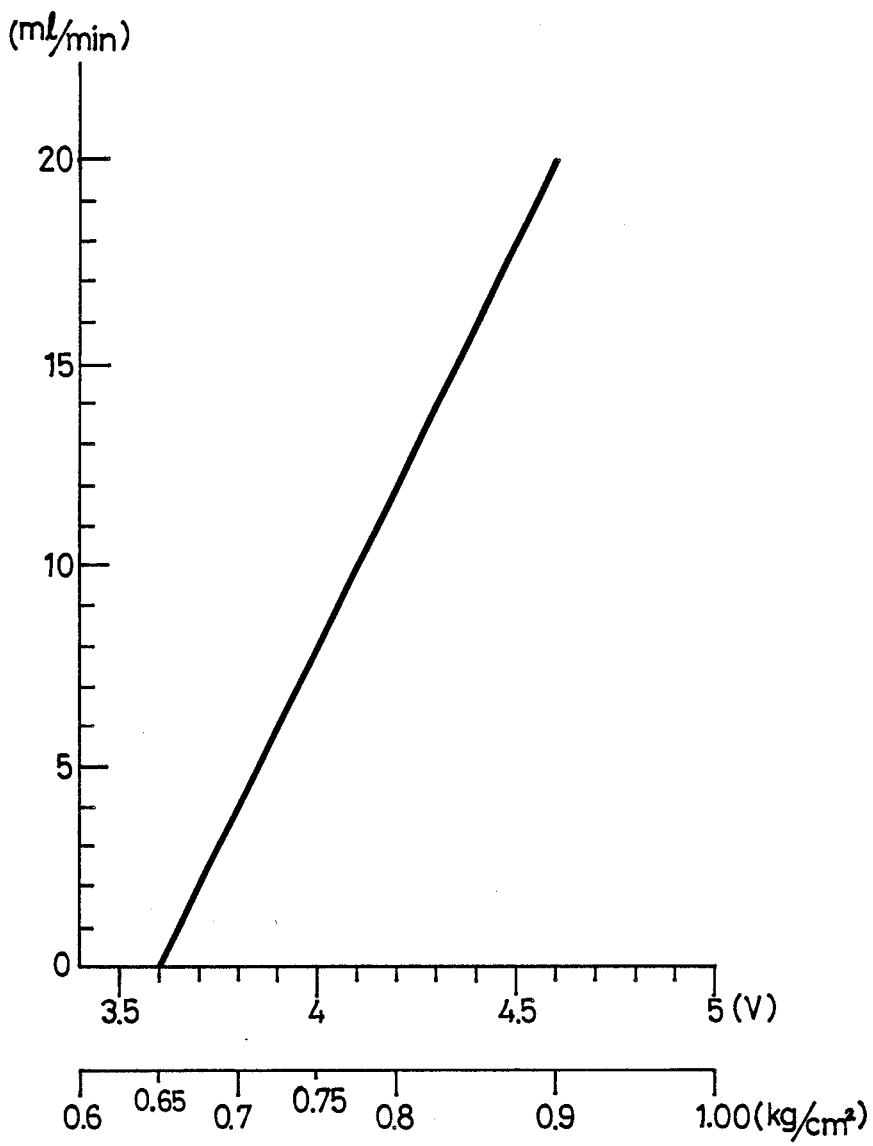
FIG. 3 is a graph showing rates of discharge from a nozzle at varying internal pressures of a supply pipe.

The rates of discharge from the nozzle 11 at varying internal pressures of the solution supply pipe 13 are actually measured by the following method. FIG. 3 shows the measurements. In FIG. 3, plotted as abscissa are the pressure acting on the sensor 17 and the voltage of the sensor 17 corresponding to the pressure, vs. the discharge rate of the nozzle 11.

The spraying air supply pipe 14 and the pressurizing air supply pipe 15 are each set to an internal pressure of 1.5 kg/cm$^2$. When the internal pressure of the pressurizing air supply pipe 15 is set to 1.5 kg/cm$^2$, a back pressure of 0.65 kg/cm$^2$ acts on the nozzle 11. Accordingly, the nozzle 11 discharges no solution if the internal pressure of the solution supply pipe 13 is up to 0.65 kg/cm$^2$. When the opening degree of the control valve 16 is increased, the pressure of the hydrogen peroxide solution acting on the nozzle 11 increases, while a decrease in the opening degree reduces the pressure. The internal pressure of the solution supply pipe 13 is varied by adjusting the opening degree of the control valve 16 to measure the discharge rates corresponding to the variations. The measurements thus obtained are shown in FIG. 3, which reveals that a variation of 0.0125 kg/cm$^2$ in the internal pressure of the solution supply pipe 13 results in a variation of 1 ml/min in the discharge rate.

Instead of measuring the discharge rate, the rate of flow through the solution supply pipe 13 may be measured. In this case, however, accurate data is not available unless the evolution of oxygen is precluded within the solution supply pipe 13.

The signal delivered from the reading means 28 of the computing unit 21 is fed to a recorder 22 and/or an indicator 23 and is recorded as operation data or shown as a flow rate. The output signal from the computing unit 21 is fed also to a comparator 24, which has another signal delivered from a setting unit 25. The setting unit 25 produces a signal in accordance with a value set for the required rate of discharge from the nozzle 11. The comparator 24 calculates the difference between the values of the two input signals and produces a signal corresponding to the difference. When the output signal of the comparator 24 represents a value other than zero, the signal means that the current discharge rate is greater or smaller than the required rate and is fed to an alarm 26 as an alarm actuating signal.

What is claimed is:

1. A spraying apparatus for recording and/or displaying the discharge rates of an aqueous solution of hydrogen peroxide sprayed therefrom, comprising:
    a tank means for storing the aqueous solution of hydrogen peroxide;

a solution supply pipe extending from said tank means;

a spray nozzle positioned on said solution supply pipe;

a valve means for controlling a flow rate of the aqueous solution;

a pressure sensor means for detecting varying internal pressures of said solution supply pipe and positioned on said solution supply pipe between said spray nozzle and said valve and in proximity with said spray nozzle;

a pressurized air supply means for supplying pressurized air both to said tank means and to said spray nozzle;

a memory means for storing comparison data of the varying internal pressures and the corresponding discharge rates;

reading means for reading the discharge rates for the varying internal pressures; and at least one of a device for recording and a device for displaying the discharge rates of the aqueous solution.

2. An apparatus as defined in claim 1, further comprising a computing unit for receiving an electric signal representing the pressure detected by the pressure sensor, wherein said computing unit includes said memory means having the relationship of the discharge rate of the nozzle with the corresponding internal pressure of the pipe and said reading means for reading from the memory means the discharge rate corresponding to a particular pressure detected by the sensor to produce an output signal, and further wherein the output signal from said reading means is fed to at least one of said device for recording and said device for displaying.

3. An apparatus as defined in claim 2 further comprising a setting unit for producing an output signal corresponding to a value set according to the required rate of discharge from said nozzle, a comparator for calculating the difference between the value of the output signal from said reading means and the output signal from said setting unit to produce an output signal corresponding to the difference, and an alarm for receiving the output signal of said comparator as an actuating signal.

4. An apparatus as defined in claim 2, wherein said pressure sensor is attached to said spray nozzle.

* * * * *